United States Patent
Sisko et al.

(10) Patent No.: US 8,759,523 B2
(45) Date of Patent: Jun. 24, 2014

(54) PROCESS FOR PREPARING PYRANO—[2,3-C]PYRIDINE DERIVATIVES

(75) Inventors: Joseph Sisko, King of Prussia, PA (US); Douglas Mans, King of Prussia, PA (US); Hao Yin, King of Prussia, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/810,741

(22) PCT Filed: Jul. 19, 2011

(86) PCT No.: PCT/US2011/044489
§ 371 (c)(1),
(2), (4) Date: Jan. 17, 2013

(87) PCT Pub. No.: WO2012/012391
PCT Pub. Date: Jan. 26, 2012

(65) Prior Publication Data
US 2013/0116436 A1  May 9, 2013

Related U.S. Application Data

(60) Provisional application No. 61/365,880, filed on Jul. 20, 2010.

(51) Int. Cl.
*C07D 513/02* (2006.01)
(52) U.S. Cl.
USPC .......................................................... 546/115
(58) Field of Classification Search
USPC .......................................................... 546/115
See application file for complete search history.

(56) References Cited

FOREIGN PATENT DOCUMENTS

WO          87/07607       12/1987

OTHER PUBLICATIONS

Goodman et al. Org.Lett. 2012, 14(6), 1604-1607.*
Padwa and Cohen, Studies Dealing with the Aza-Claisen Rearrangement of 2-Allyloxy-Substituted Oxazoles, Journal of Organic Chemistry (1984) 49(3):399-406.
Billeret, et al., Syntheses of Chromenes and Azachromenes: 2H-1 Benzopyran, 2H-Pyrano[3,2-b]pyridine, 2H- Pyrano[2,3-c]pyridine, and Derivatives, Synthesis (1993) 9:881-884.
Ohba, et al., Intramolecular Diels-Alder reactions of oxazole-olefins: synthesis of Rauwolfia alkaloids suaveoline and norsuaveoline, Tetrahedron (2007) 63(41):10337-10344.
Search and Examination Report from Singapore dated Nov. 8, 2013, received Nov. 26, 2013.
Martin, et al., A Convenient, One Step Synthesis of Pyranol[2,3-b]Pyridines, Tetrahedron 1988 vol. 44(18): 5861-5868.
Williams, et al., Studies of Stereocontrolled Allylation Reactions for the Total Synthesis of Phorboxazole A, PNAS 2004, vol. 101(33): 12058-12063.
Movassaghi, et al., A Versatile Cyclodehydration Reaction for the Synthesis of Isoquinoline and Beta-Carboline Derivatives, Org Lett 2008, vol. 10(16): 1-12 [pp. 3485-3488], Abstract. Downloaded from http://www.ncbi.nlm.nih.gov/prnc/articles/PMC2692836/pdf/nihms-108650.pdf.

* cited by examiner

*Primary Examiner* — Nizal Chandrakumar
(74) *Attorney, Agent, or Firm* — Robert H. Brink

(57) ABSTRACT

The present invention relates to a process comprising the step of dehydrating a compound of Formula (I):

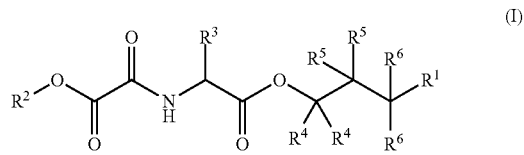

with a suitable dehydrating reagent to form a compound of Formula (II):

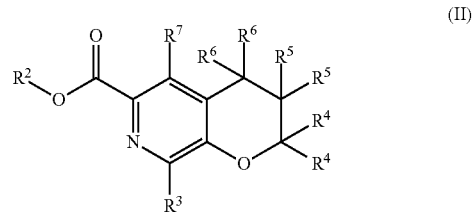

wherein $R^1$-$R^7$ are as defined herein.
Compounds of Formula (II) have shown promise as intermediates to compounds useful for treating bacterial infections.

21 Claims, No Drawings

PROCESS FOR PREPARING PYRANO—[2,3-C]PYRIDINE DERIVATIVES

This application is filed pursuant to 35 U.S.C. §371 as a United States National Phase Application of International Patent Application Serial No. PCT/US2011/044489 filed Jul. 19, 2011, which claims priority to U.S. Application No. 61/365,880 filed Jul. 20, 2010, the contents of each of the foregoing applications are hereby incorporated by reference.

BACKGROUND OF THE INVENTION

The present invention relates to pyrano-[2,3-c]pyridine derivatives and methods for their preparation. 3,4-Dihydro-2H-pyrano[2,3-c]pyridine-6-carbaldehyde, disclosed in WO2004058144, is characterized by the following Formula (VIII):

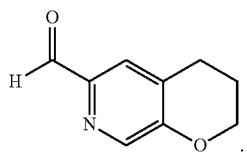

Pyrano-[2,3-c]pyridine derivatives have shown promise as useful intermediates to compounds useful for treating bacterial infections. Previously disclosed methods for preparing pyrano-[2,3-c]pyridine-6-carbaldehyde are arduous, requiring many steps using expensive starting materials and resulting in unsatisfactory overall yields. (See WO2003042210, Example 18; WO2004058144, Example 126(a)-(e)) It would therefore be advantageous to discover alternative ways of preparing this building block from relatively inexpensive chemicals.

SUMMARY OF THE INVENTION

In one aspect, the present invention is a process comprising dehydrating a compound of Formula (I):

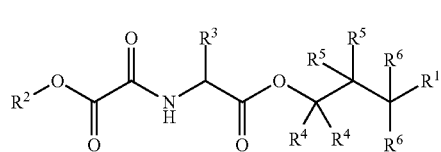

with a suitable dehydrating reagent to form a compound of Formula (II):

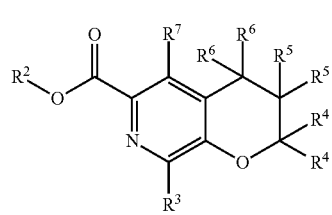

wherein $R^1$ is —CH=CH—$R^8$ or —CH$_2$—CH=CH—$R^9$;
$R^2$ is $C_1$-$C_4$-alkyl;
$R^3$ is H, $C_1$-$C_4$-alkyl, benzyl, -phenyl-($R^{10}$)$_x$, or —$C_1$-$C_4$-alkyl-COO—$C_1$-$C_4$-alkyl;
each $R^4$ is independently H, or $C_1$-$C_4$-alkyl;
each $R^5$ and each $R^6$ are independently H, $C_1$-$C_4$-alkyl, —O—$C_1$-$C_4$-alkyl, or —S—$C_1$-$C_4$-alkyl;
$R^7$ is $R^8$ or —CH$_2$—$R^9$;
$R^8$ is H, $C_1$-$C_4$-alkyl, -phenyl-($R^{10}$)$_x$, or —COO—$C_1$-$C_4$-alkyl;
$R^9$ is H, $C_1$-$C_3$-alkyl, -phenyl-($R^{10}$)$_x$, or —COO—$C_1$-$C_4$-alkyl;
each $R^{10}$ is independently halo, $C_1$-$C_4$-alkyl, —O—$C_1$-$C_6$-alkyl, or —S—$C_1$-$C_4$-alkyl; and
each x is independently 0, 1, or 2.

In another aspect, the present invention is a process comprising the step of dehydrating a compound of Formula (V):

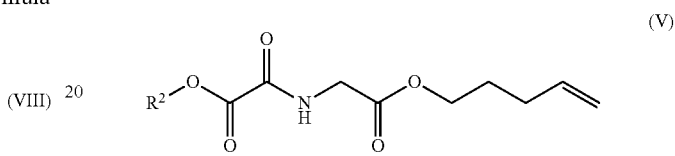

with a suitable dehydrating reagent to form a compound of Formula (VI):

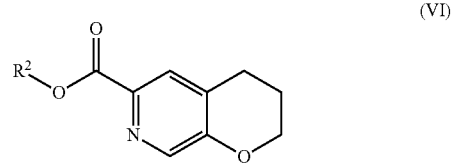

wherein $R^2$ is $C_1$-$C_4$-alkyl. Compounds of Formula (II) have shown promise as intermediates to compounds useful for treating bacterial infections.

DETAILED DESCRIPTION OF THE INVENTION

In a first aspect, the present invention is a process comprising dehydrating a compound of Formula (I):

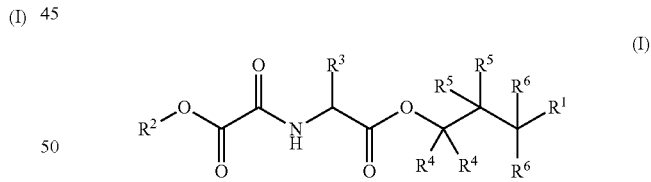

with a suitable dehydrating reagent to form a compound of Formula (II):

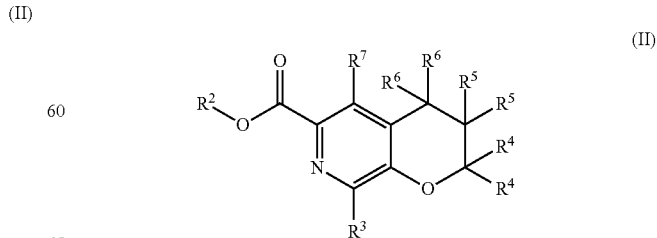

wherein $R^1$-$R^7$ are as previously defined.

$C_1$-$C_4$-alkyl is used herein to refer to a straight chain or branched alkyl group with up to four carbon atoms. Examples include methyl, ethyl, n-propyl, isopropyl, n-butyl, sec-butyl, and t-butyl.

Similarly, $C_1$-$C_3$-alkyl refers to methyl, ethyl, n-propyl, or isopropyl.

In another embodiment, $R^4$, $R^5$, and $R^6$ are each independently H or $C_1$-$C_4$-alkyl.

In another embodiment, $R^4$, $R^5$, and $R^6$ are each independently H or methyl.

In another embodiment, each of $R^4$, $R^5$, and $R^6$ is H.

Examples of suitable dehydrating reagents include trifluoromethanesulfonic anhydride ($Tf_2O$) and phosphorus pentoxide ($P_2O_5$), preferably $Tf_2O$. The reaction of Compound (I) to Compound (II) [or Compound (V) to Compound (VI)] is advantageously carried out in the presence of a suitable base, preferably an organic base such as pyridine, triethylamine, or diisopropylethylamine Preferably, the base is used in a range of from 1 equivalent with respect to Compound (I) to less than the amount, in equivalents, of the dehydrating reagent.

A compound of Formula (Ia):

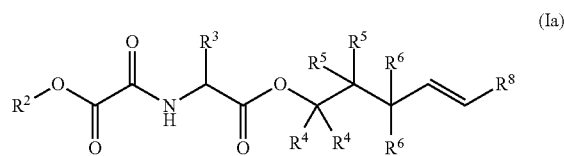

(Ia)

can be prepared, for example, by reaction of Cl—CO—$CO_2$—$R^2$ with a compound of Formula (4):

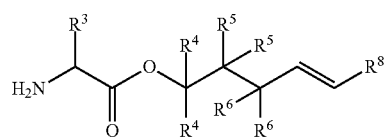

(4)

in the presence of a suitable base, preferably an organic base, where $R^8$ is as previously defined.

The compound of Formula (4) can be prepared by deprotecting a compound of Formula (3):

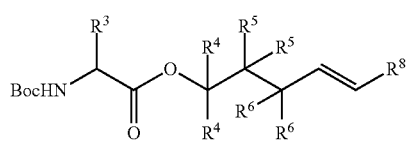

(3)

under suitable deprotecting conditions, preferably by reaction with a strong acid, such as HCl, $H_2SO_4$, MsOH or TsOH.

The compound of Formula (3) can be prepared by condensing a compound of Formula (1):

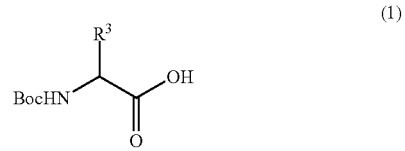

(1)

with a compound of Formula (2):

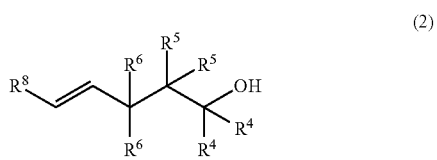

(2)

under suitable condensation conditions, for example, in the presence of 1,1'-carbonyldiimidazole.

A compound of Formula (Ib):

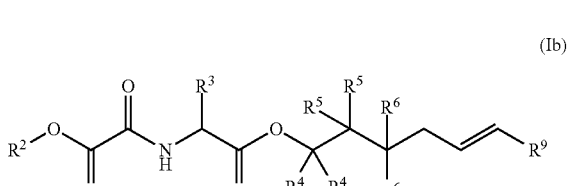

(Ib)

can be prepared in a similar manner to the compound of Formula (Ia), where $R^9$ is as previously defined.

The compound of Formula (II):

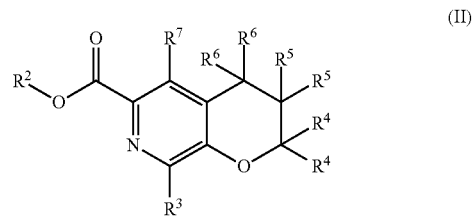

(II)

can be contacted with a suitable reducing reagent to form a compound of Formula (III):

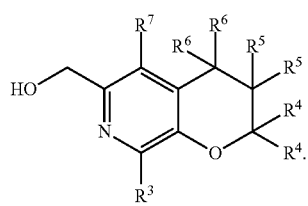

(III)

Examples of suitable reducing reagents include diisobutylaluminium hydride, $LiAlH_4$, $LiBH_4$, and $NaBH_4$.

The compound of Formula (III) can be contacted with a suitable oxidizing reagent to form a compound of Formula (IV):

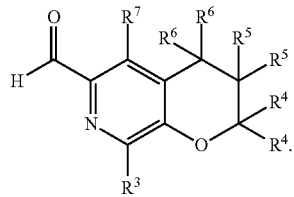

Examples of suitable oxidizing reagents include $MnO_2$, Swern oxidation reagents, 2-iodoxybenzoic acid, pyridine sulphur trioxide, and Dess-Martin periodinane. Alternatively, the compound of Formula (IV):

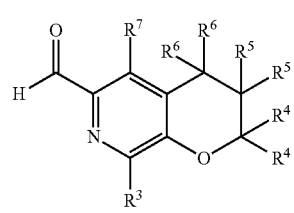

can be prepared by reducing the compound of Formula (II):

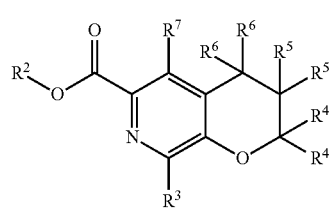

with a suitable reducing reagent, such as diisobutylaluminium hydride.

Schemes

Scheme 1 illustrates one aspect of the present invention. Compound (3) can be prepared by contacting acid (1) with alcohol (2) under suitable condensation conditions, for example, in the presence of 1,1'-carbonyldiimidazole. The protecting group is removed from compound (3) to form amine (4) under suitable deprotecting conditions, preferably by reaction with a strong acid, such as HCl, $H_2SO_4$, MsOH or TsOH.

The compound of Formula (Ia) can be prepared by contacting amine (4) with $X$—$CO$—$CO_2$—$R^2$ (X=halo or —$OCH_3$) in the presence of a suitable base, preferably, an organic base such as triethylamine.

The compound of Formula (IIa) can be prepared by treatment of the compound of Formula (Ia) with suitable base and dehydrating reagent, for example, pyridine and $Tf_2O$.

The compound of Formula (IVa) can be prepared in at least two ways. For example, the compound of Formula (IIa) can be reduced to alcohol (IIIa) using a suitable reducing reagent such as diisobutylaluminium hydride, $LiAlH_4$, $LiBH_4$, or $NaBH_4$. Alcohol (IIIa) can then be oxidized to form the compound of Formula (IVa) using a suitable oxidizing reagent such as $MnO_2$, Swern oxidation reagents, 2-iodoxybenzoic acid, pyridine sulphur trioxide, or Dess-Martin periodinane.

Alternatively, the compound of Formula (IIa) can be reduced to form the compound of Formula (IVa) using a suitable reducing reagent such as diisobutylaluminium hydride.

Scheme 1

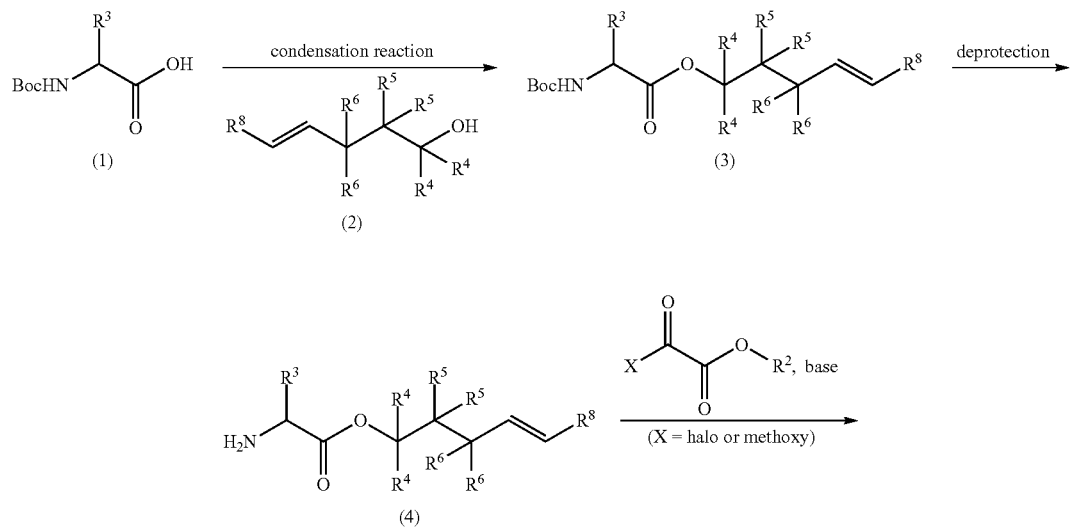

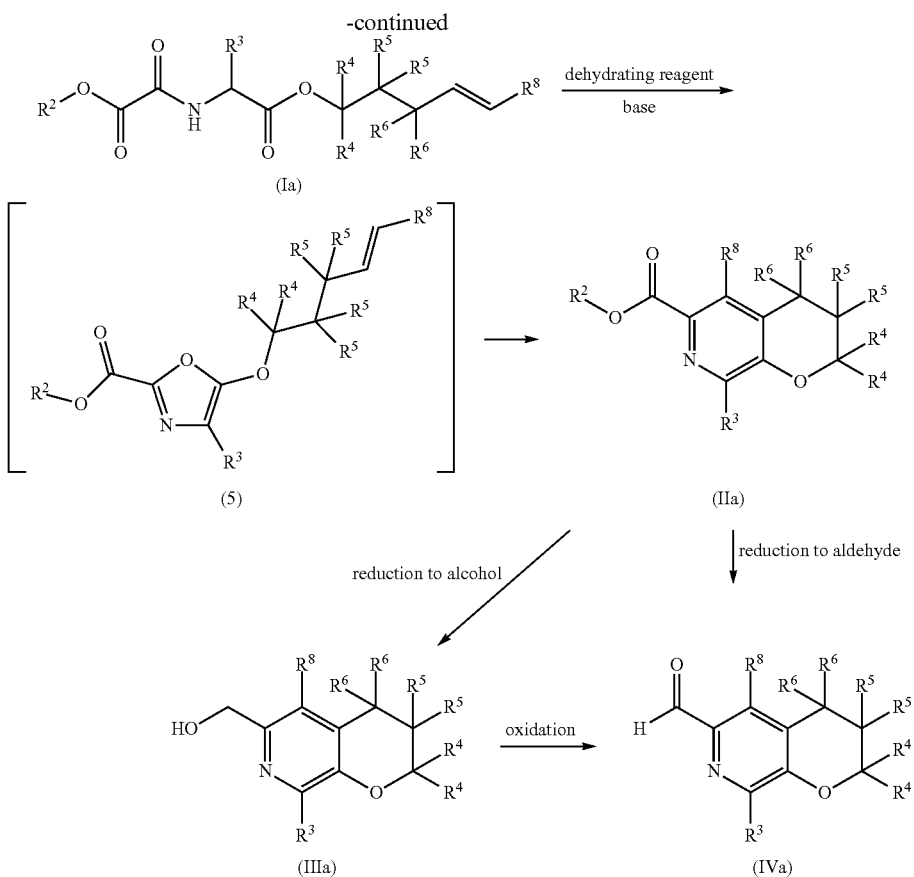
Another embodiment of the present invention is illustrated in Scheme 2. The compound of Formula (IVb) can be prepared in a similar manner as the compounds in Scheme 1 starting from alcohol (6).
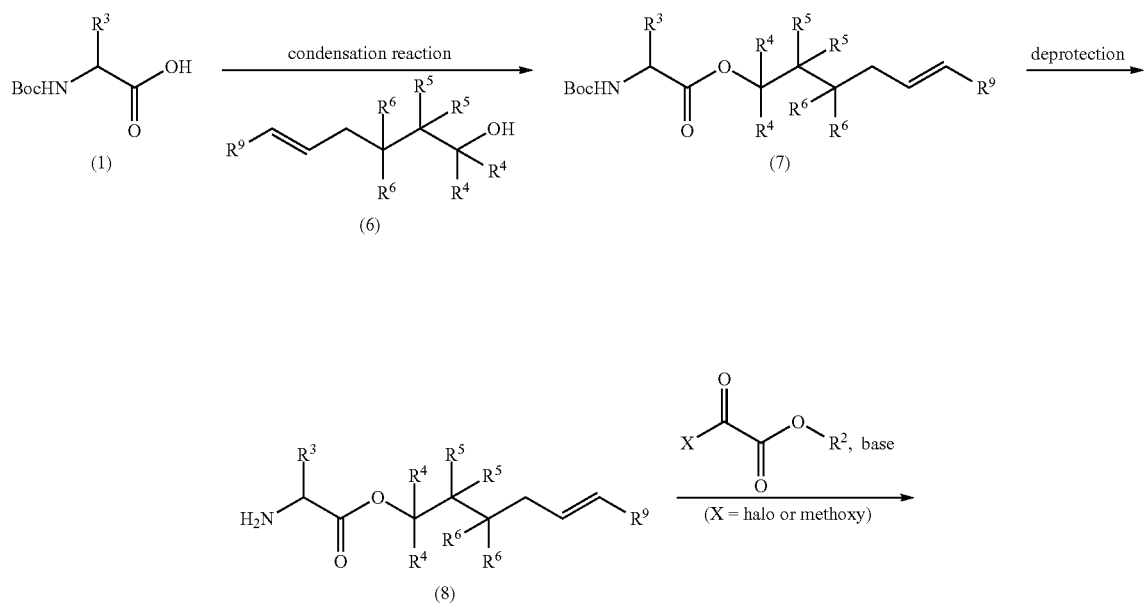

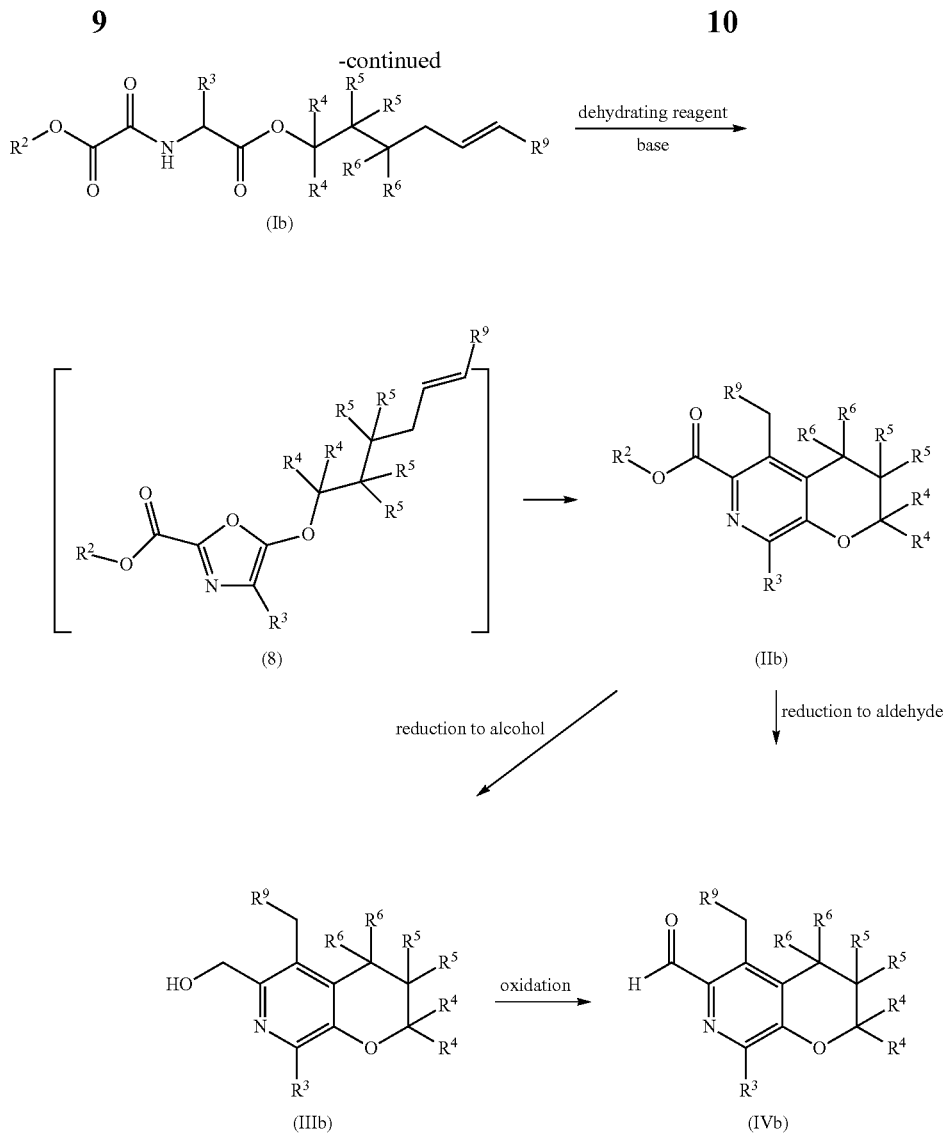

EXAMPLES

The following examples are illustrative of the process of the present invention and are not intended to limit the scope of the invention.

Example 1

Methyl 3,4-dihydro-2H-pyrano[2,3-c]pyridine-6-carboxylate

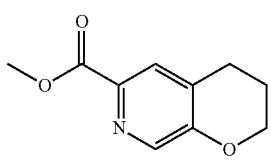

(a) Methyl 2-oxo-2-((2-oxo-2-(pent-4-en-1-yloxy)ethyl)amino)acetate

To a 1-L reactor was charged 1,1'-carbonyldiimidazole (CDI) (44.0 g, 0.95 eq) and tert-butyl methyl ether (TBME) (150 mL). The mixture was heated with stirring to ~40° C. whereupon a solution of N-Boc-glycine (50 g, 1 eq) in TBME (200 mL) was added and stirring continued for 0.5 h. Pent-4-en-1-ol (23 g, 0.95 eq) was then added over 30 min and stirring was continued at 40° C. for 2 h then cooled to 20° C. 1N HCl (125 mL) was added to form a biphasic mixture. The layers were separated and the organic layer was washed with 1N HCl (1×125 mL) followed by water (1×125 mL). The TBME was distilled off and the crude pent-4-en-1-yl2-((tert-butoxycarbonyl)amino)acetate was then azeotropically dried with toluene (200 mL). The mixture was heated to 40° C. and sufficient toluene was added to bring the total volume of toluene to ~200 mL. Methanesulfonic acid (34 g, 1.25 eq) was added and the mixture was stirred at 40° C. for 2 h then cooled to 20° C. The mixture was then transferred into a vessel containing dimethyl oxalate (34 g, 1 eq) and the temperature of the vessel was maintained at 20° C. with stirring. Triethylamine (43 g, 1.5 eq) was then added to this mixture stirring was continued for a further 1 h. The mixture was washed with water (125 mL). The toluene solution was concentrated with azeotropic drying to give methyl 2-oxo-2-((2-oxo-2-(pent-4-en-1-yloxy)ethyl)amino)acetate as an oil. $^1$H NMR (400 MHz, CDCl$_3$) δ ppm 7.55 (s, 1H), 5.73-5.86 (m, 1H), 4.97-5.10 (m, 2H), 4.21 (t, J=6.65 Hz, 2H), 4.13 (d, J=5.52 Hz, 2H), 3.93 (s, 3H), 2.13 (q, J=7.42 Hz, 2H), 1.71-1.85 (m, 2H); $^{13}$C NMR (75 MHz, CDCl$_3$) δ ppm 168.58, 160.35, 156.29, 137.05, 115.56, 65.25, 53.72, 41.48, 29.84, 27.56; HRMS (M+Na) m/z, calcd for C$_{10}$H$_{15}$NO$_5$Na, 252.0848; found, 252.0852.

(b) The Title Compound

Methyl 2-oxo-2-((2-oxo-2-(pent-4-en-1-yloxy)ethyl) amino)acetate (42.5 g, 1 eq) and dichloromethane (DCM) (425 mL) were added to a vessel with stirring followed by the addition of pyridine (17.6 g, 1.2 eq). Tf$_2$O (78.5 g, 1.5 eq) was added over 45 min to the mixture maintaining an internal temperature of ~25° C. The mixture was stirred for 6 h at which point the reaction was carefully quenched by the addition of 20 wt % aqueous NaOAc (255 mL) to form a biphasic solution. The aqueous layer was extracted with DCM (85 mL). The combined organic layers were washed first with water (127.5 mL) and 10 wt % citric acid solution (170 mL). 6N HCl (127.5 mL) was added to the mixture to form a biphasic mixture. The two layers were separated and the organic layer was extracted with 6 N HCl (85 mL). The acidic aqueous layers were combined and DCM (127.5 mL) was added. While maintaining the temperature below 25° C., 28 wt % aqueous NH$_4$OH was slowly added until the pH of the aqueous layer reached 3-5. The two layers were separated and the aqueous layer was extracted with DCM (85 mL). The combined organic layers were washed with water (85 mL). The organic solution was concentrated under reduced pressure to provide the title compound as an oil which solidified on standing. $^1$H NMR (400 MHz, CDCl$_3$) δ ppm 8.17 (s, 1H), 7.80-7.86 (m, 1H), 4.26 (t, J=5.19 Hz, 2H), 3.92 (s, 3H), 2.79 (t, J=6.44 Hz, 2H), 1.97-2.09 (m, 2H); $^{13}$C NMR (75 MHz, CDCl$_3$) δ ppm 165.11, 154.25, 138.95, 138.64, 130.06, 126.13, 65.55, 51.99, 23.57, 20.67; HRMS (M+Na) m/z, calcd for C$_{10}$H$_{11}$NO$_3$Na, 216.0637; found, 216.0643.

Example 2

Ethyl 8-methyl-3,4-dihydro-2H-pyrano[2,3-c]pyridine-6-carboxylate

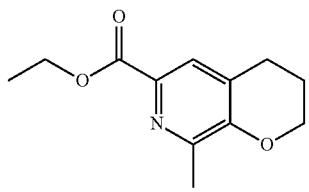 [SMILES: CCOC(=O)c1cc2c(c(C)n1)OCCC2]

(a) Pent-4-en-1-yl 2-(2-ethoxy-2-oxoacetamido)propanoate

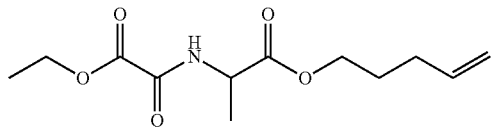 [SMILES: C=CCCCOC(=O)C(C)NC(=O)C(=O)OCC]

N-(t-Butoxycarbonyl)alanine (3.1 g, 1 eq) and DCM (50 mL) were added to a vessel with stirring followed by the addition of CDI (3.1 g, 1.15 eq). The mixture was stirred at ambient temperature for 18 h after which time 4-penten-1-ol (1.8 g, 1.25 eq) was added. The mixture was stirred a further 18 h at ambient temperature at which point the reaction was quenched with 1N HCl. A biphasic mixture was formed and the layers were separated. The organic layer was washed with saturated aqueous NaHCO$_3$ solution and then concentrated to give pent-4-en-1-yl 2-((tert-butoxycarbonyl)amino)propanoate as an oil. The oil was dissolved in DCM (50 mL) and methanesulfonic acid (2.2 g, 1.4 eq) was added. The mixture was stirred at ambient temperature for ~22 h then cooled in an ice/water bath. Ethyl 2-chloro-2-oxoacetate (3.4 g, 1.5 eq) was added followed by drop-wise addition of triethylamine (5.0 g, 3 eq). The mixture was stirred for 7 h after which time the reaction was quenched by 1N HCl to form a biphasic mixture. The layers were separated and the organic layer was washed with a saturated aqueous NaHCO$_3$ solution. The organic layer was then concentrated under reduced pressure to provide pent-4-en-1-yl 2-(2-ethoxy-2-oxoacetamido)propanoate as a yellow oil. $^1$H NMR (400 MHz, CDCl$_3$) δ ppm 7.64 (d, J=6.94 Hz, 1H), 5.66-5.83 (m, 1H), 4.90-5.05 (m, 2H), 4.49-4.62 (m, 1H), 4.31 (qd, J=7.17, 2.26 Hz, 2H), 4.13 (td, J=6.59, 2.13 Hz, 2H), 2.02-2.14 (m, 2H), 1.67-1.78 (m, 2H), 1.44 (d, J=7.19 Hz, 3H), 1.34 (t, J=7.15 Hz, 3H); $^{13}$C NMR (75 MHz, CDCl$_3$) δ ppm 171.64, 159.94, 155.83, 136.94, 115.40, 64.98, 63.10, 48.40, 29.71, 27.44, 17.88, 13.80; HRMS (M+Na) m/z, calcd for C$_{12}$H$_{19}$NO$_5$Na, 280.1161; found, 280.1166.

(b) The Title Compound

Pent-4-en-1-yl2-(2-ethoxy-2-oxoacetamido)propanoate (1.05 g, 1 eq) and DCM (15 mL) were added to a vessel with stirring. Pyridine (0.39 g, 1.2 eq) was then added and the mixture was cooled to 15° C. Tf$_2$O (1.7 g, 1.5 eq) was added to the mixture over 15 min and the mixture was warmed to ambient temperature to stir for 1.5 h. The reaction was quenched by the addition of DCM and 20 wt % aqueous NaOAc to form a biphasic mixture. The layers were separated and the organic layer was washed with water. The organic layer was then concentrated under reduced pressure to provide the title compound as yellow solid. $^1$H NMR (300 MHz, CDCl$_3$) δ ppm 7.62 (s, 1H), 4.32 (q, J=7.12 Hz, 2H), 4.16-4.25 (m, 2H), 2.70 (t, J=6.44 Hz, 2H), 2.37 (s, 3H), 1.86-2.03 (m, 2H), 1.31 (t, J=7.12 Hz, 3H); $^{13}$C NMR (75 MHz, CDCl$_3$) δ ppm 165.15, 152.44, 147.98, 137.72, 128.73, 124.80, 66.85, 61.09, 23.98, 21.06, 18.98, 14.11; HRMS (M+H) m/z, calcd for $C_{12}H_{16}NO_3$, 222.1130; found, 222.1133.

Example 3

Ethyl 8-benzyl-3,4-dihydro-2H-pyrano[2,3-c]pyridine-6-carboxylate

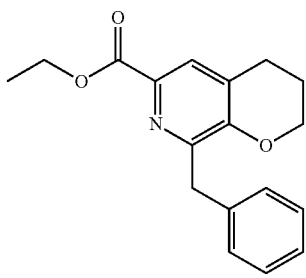 [SMILES: CCOC(=O)c1cc2c(c(Cc3ccccc3)n1)OCCC2]

(a) Pent-4-en-1-yl 2-(2-ethoxy-2-oxoacetamido)-3-phenylpropanoate

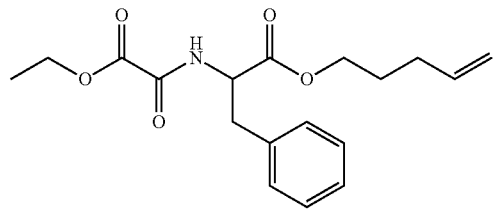 [SMILES: C=CCCCOC(=O)C(Cc1ccccc1)NC(=O)C(=O)OCC]

Pent-4-en-1-yl 2-(2-ethoxy-2-oxoacetamido)-3-phenylpropanoate was prepared in a similar manner as Example 2(a) starting with N-(t-butoxycarbonyl)phenylalanine (1.0 g). $^1$H NMR (400 MHz, CDCl$_3$) δ ppm 7.52 (d, J=8.03 Hz, 1H), 7.28-7.37 (m, 3H), 7.15-7.19 (m, 2H), 5.73-5.84 (m, 1H), 5.06-5.10 (m, 1H), 5.01-5.05 (m, 1H), 4.87-4.95 (m, 1H), 4.38 (qd, J=7.15, 1.72 Hz, 2H), 4.11-4.21 (m, 2H), 3.21 (d, J=6.11 Hz, 2H), 2.05-2.13 (m, 2H), 1.69-1.79 (m, 2H), 1.41 (t, J=7.15 Hz, 3H); $^{13}$C NMR (75 MHz, CDCl$_3$) δ ppm 170.30, 159.85, 155.93, 137.01, 135.14, 129.10, 128.62, 127.26, 115.43, 65.10, 63.22, 53.57, 37.70, 29.75, 27.42, 13.85; HRMS (M+H) m/z, calcd for $C_{18}H_{24}NO_5$, 334.1654; found 334.1665.

(b) The Title Compound

Pent-4-en-1-yl 2-(2-ethoxy-2-oxoacetamido)-3-phenylpropanoate (0.80 g, 1 eq) and DCM (15 mL) were added to a vessel with stirring. Pyridine (0.23 g, 1.2 eq) was then added and the mixture was cooled to 15° C. Tf$_2$O (1.0 g, 1.5 eq) was added to the mixture over 15 min and the mixture was warmed to ambient temperature. The solution was stirred for 3.5 h after which time the reaction was quenched by DCM and 20 wt % aqueous NaOAc to form a biphasic mixture. The layers were separated and the organic layer was extracted with 6N HCl (3×10 mL). The combined acid layers were washed with DCM and the pH was adjusted to ~9 with solid K$_2$CO$_3$. The basic aqueous layer was extracted with DCM. The organic layer was concentrated under reduced pressure to provide the title compound. $^1$H NMR (300 MHz, CDCl$_3$) δ ppm 7.74 (s, 1H), 7.10-7.35 (m, 5H), 4.43 (q, J=7.12 Hz, 2H), 4.22-4.29 (m, 2H), 4.21 (s, 2H), 2.78 (t, J=6.41 Hz, 2H), 1.93-2.06 (m, 2H), 1.41 (t, J=7.12 Hz, 3H); $^{13}$C NMR (75 MHz, CDCl$_3$) δ ppm 165.08, 152.25, 149.62, 138.86, 138.06, 129.62, 128.61, 127.80, 125.61, 125.23, 66.70, 60.97, 38.55, 23.93, 20.92, 14.10; HRMS (M+H) m/z, calcd for $C_{18}H_{20}NO_3$, 298.1443; found 298.1450.

Example 4

Ethyl 8-phenyl-3,4-dihydro-2H-pyrano[2,3-c]pyridine-6-carboxylate

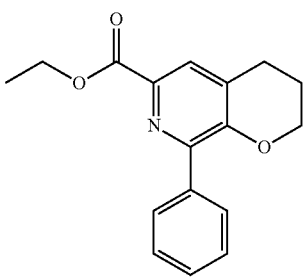 [SMILES: CCOC(=O)c1cc2c(c(-c3ccccc3)n1)OCCC2]

(a) Ethyl 2-oxo-2-((2-oxo-2-(pent-4-en-1-yloxy)-1-phenylethyl)amino)acetate

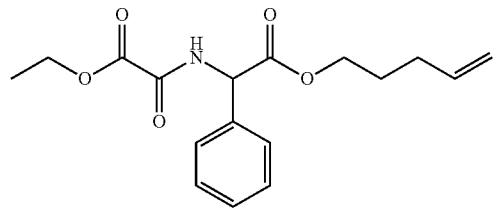 [SMILES: C=CCCCOC(=O)C(NC(=O)C(=O)OCC)c1ccccc1]

Ethyl 2-oxo-2-((2-oxo-2-(pent-4-en-1-yloxy)-1-phenylethyl)amino)acetate was prepared in a similar manner as Example 2(a) starting from α-[[(1,1-dimethylethoxy)carbonyl]amino]-benzeneacetic acid (0.96 g). $^1$H NMR (400 MHz, CDCl$_3$) δ ppm 8.01 (d, J=7.11 Hz, 1H), 7.32-7.43 (m, 5H), 5.63-5.78 (m, 1H), 5.58 (d, J=7.61 Hz, 1H), 4.88-4.98 (m, 2H), 4.36 (q, J=7.11 Hz, 2H), 4.11-4.24 (m, 2H), 1.93-2.04 (m, 2H), 1.70 (qd, J=7.12, 6.88, 2.05 Hz, 2H), 1.39 (t, J=7.15 Hz, 3H); $^{13}$C NMR (75 MHz, CDCl$_3$) δ ppm 169.75, 159.93, 155.72, 136.94, 135.47, 129.02, 128.83, 127.26, 115.53, 65.40, 63.32, 56.69, 29.63, 27.44, 13.91; HRMS (M+H) m/z, calcd for $C_{17}H_{22}NO_5$, 320.1498; found 320.1512.

(b) The Title Compound

Ethyl 8-phenyl-3,4-dihydro-2H-pyrano[2,3-c]pyridine-6-carboxylate was prepared in a similar manner as Example 3(b) starting from ethyl 2-oxo-2-((2-oxo-2-(pent-4-en-1-yloxy)-1-phenylethyl)amino)acetate (0.91 g). $^1$H NMR (300 MHz, CDCl$_3$) δ ppm 7.91-7.98 (m, 2H), 7.84 (s, 1H), 7.34-7.49 (m, 3H), 4.44 (q, J=7.12 Hz, 2H), 4.29-4.38 (m, 2H), 2.91 (t, J=6.44 Hz, 2H), 2.02-2.18 (m, 2H), 1.43 (t, J=7.12 Hz, 3H); $^{13}$C NMR (75 MHz, CDCl$_3$) δ ppm 165.11, 152.06, 149.30, 146.60, 138.65, 136.72, 135.82, 130.64, 129.30, 128.06, 127.59, 125.48, 66.89, 61.07, 24.37, 20.84, 14.09; HRMS (M+H) m/z, calcd for $C_{17}H_{18}NO_3$, 284.1287; found 284.1301.

Example 5

Methyl 5-methyl-3,4-dihydro-2H-pyrano[2,3-c]pyridine-6-carboxylate

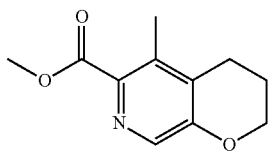

(a) (E)-Methyl 2-((2-(hex-4-en-1-yloxy)-2-oxoethyl)amino)-2-oxoacetate

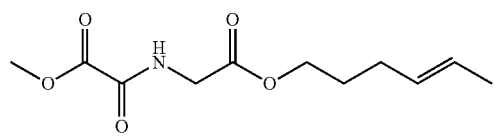 [SMILES: C/C=C/CCCOC(=O)CNC(=O)C(=O)OC]

To a vessel maintained at 40° C. was charged CDI (2.75 g, 0.95 eq) and TBME (9 mL). To this mixture was added with stirring a solution of N-(t-butoxycarbonyl)glycine (3.1 g, 1.0 eq) dissolved in TBME (12 mL) over 30 min. Stirring was continued for an additional 30 min, whereupon trans-4-hexen-1-ol (1.7 g, 0.95 eq) was added over 30 min. The mixture was maintained with stirring at 40° C. for an additional 3.5 h, then cooled to ambient temperature and stirred a further 14 h. The mixture was washed with 1N HCl (2×7.8 mL) then water (1×7.8 mL). The organic layer was dried over $Na_2SO_4$, filtered and concentrated to give (E)-hex-4-en-1-yl2-((tert-butoxycarbonyl)amino)acetate as an oil. The oil was dissolved in DCM (12 mL) and 4.0 M HCl in dioxane (2.8 mL) was added drop-wise. The mixture was stirred at ambient temperature for 1.5 h then the mixture was heated to 35° C. and stirred for 3 h. 4.0 M HCl in dioxane (2.8 mL) was added drop-wise. After 6 h at 35° C. a further dose of 4.0 M HCl in dioxane (2.8 mL) was added drop-wise and the mixture was stirred for a further 4 h. The mixture was cooled to ambient temperature and the solvent was removed under reduced pressure. A portion of the residue (1.0 g) was dissolved in DCM (8 mL) and methyl 2-chloro-2-oxoacetate (0.63 g) was added. Triethylamine (1.0 g) was added drop-wise over 20 min. The mixture was stirred for 1 h before being quenched by 1N HCl (2.5 mL) to form a biphasic mixture. The layers were separated and the organic layer was washed with 1N HCl (1×2.5 mL), water (1×2.5 mL) and concentrated under reduced pressure to provide an oil. Flash column chromatography ($SiO_2$, 10→60% EtOAc/Hex gradient) provided the title compound as an oil as a 95:5 mixture of trans:cis isomers. $^1$H NMR (300 MHz, $CDCl_3$) δ ppm 7.57 (s, 1H), 5.31-5.55 (m, 2H), 4.17 (t, J=6.69 Hz, 2H), 4.12 (d, J=5.51 Hz, 2H), 3.92 (s, 3H), 1.97-2.10 (m, 2H), 1.67-1.77 (m, 2H), 1.62-1.67 (m, 3H); $^{13}$C NMR (75 MHz, $CDCl_3$) δ ppm 168.60, 160.35, 156.28, 129.49, 126.12, 65.34, 53.68, 41.47, 28.62, 28.17, 17.84; HRMS (M+H) m/z, calcd for $C_{11}H_{18}NO_5$, 244.1185; found 244.1187.

(b) The Title Compound (E)-Methyl 2-((2-(hex-4-en-1-yloxy)-2-oxoethyl)amino)-2-oxoacetate (0.24 g, 1 eq) and DCM (2.4 mL) were added to a vessel with stirring followed by the addition of pyridine (95 mg, 1.2 eq). $Tf_2O$ (0.42 g, 1.5 eq) was then added over 45 min at ambient temperature and the mixture was stirred at ambient temperature for 48 h. The mixture was washed with 20 wt % aqueous NaOAc (2×1.5 mL), 10 wt % aqueous citric acid (3×1.5 mL), and water (1×1.5 mL). The organic layer was then concentrated under reduced pressure to provide the title compound as a solid. $^1$H NMR (300 MHz, $CDCl_3$) δ ppm 8.10 (s, 1H), 4.15-4.25 (m, 2H), 3.94 (s, 3H), 2.71 (t, J=6.56 Hz, 2H), 2.47 (s, 3H), 2.00-2.18 (m, 2H); $^{13}$C NMR (75 MHz, $CDCl_3$) δ ppm 166.71, 153.50, 138.69, 136.72, 135.67, 130.36, 65.93, 52.35, 22.18, 21.49, 14.57; HRMS (M+H) m/z, calcd for $C_{11}H_{14}NO_3$, 208.0974; found 208.0981.

Example 6

Ethyl 5-methyl-3,4-dihydro-2H-pyrano[2,3-c]pyridine-6-carboxylate

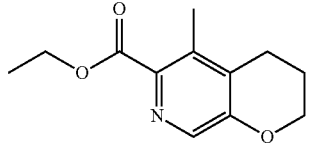 [SMILES: CCOC(=O)c1ncc2c(c1C)CCCO2]

(a) Ethyl 2-((2-(hex-5-en-1-yloxy)-2-oxoethyl)amino)-2-oxoacetate

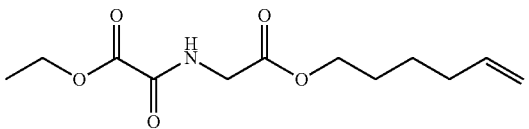 [SMILES: C=CCCCCOC(=O)CNC(=O)C(=O)OCC]

Ethyl 2-((2-(hex-5-en-1-yloxy)-2-oxoethyl)amino)-2-oxoacetate was prepared in a similar manner as Example 2(a) starting from N-(t-butoxycarbonyl)glycine (2.8 g) and 5-hexen-1-ol (2.08 g). $^1$H NMR (300 MHz, $CDCl_3$) δ ppm 7.60 (s, 1H), 5.66-5.86 (m, 1H), 4.88-5.06 (m, 2H), 4.35 (q, J=7.12 Hz, 2H), 4.17 (t, J=6.63 Hz, 2H), 4.11 (d, J=5.57 Hz, 2H), 2.06 (q, J=7.16 Hz, 2H), 1.59-1.72 (m, 2H), 1.39-1.51 (m, 2H), 1.37 (t, J=7.15 Hz, 3H); $^{13}$C NMR (75 MHz, $CDCl_3$) δ ppm 168.67, 159.84, 156.57, 138.00, 114.93, 65.66, 63.25, 41.41, 33.07, 27.77, 24.91, 13.88; HRMS (M+H) m/z, calcd for $C_{12}H_{20}NO_5$, 258.1341; found 258.1349.

(b) The Title Compound (A)

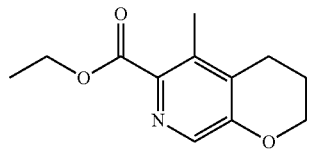

A

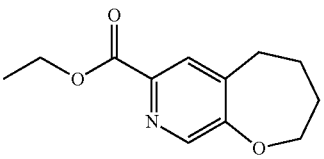

B

3:1

Ethyl-2-((2-(hex-5-en-1-yloxy)-2-oxoethyl)amino)-2-oxoacetate (0.35 g) and DCM (4 mL) were added to a vessel with stirring followed by the addition of pyridine (0.13 g). Tf$_2$O (0.58 g) was then added to the mixture slowly at ambient temperature. The mixture was stirred at ambient temperature for 4 days after which time the mixture was extracted with 6N HCl (3×10 mL). The combined acid layers were washed with DCM (10 mL) and the pH was adjusted to ~10 with solid K$_2$CO$_3$. The basic aqueous layer was extracted with DCM (20 mL). The organic layer was concentrated under reduced pressure to provide the title compound (A) and ethyl 2,3,4,5-tetrahydrooxepino[2,3-c]pyridine-7-carboxylate (B) as a 3:1 mixture as based on NMR analysis. $^1$H NMR (300 MHz, CDCl$_3$) δ ppm 8.38 (s, 0.3H, cmpd B), 8.11 (s, 1H, cmpd A), 7.95 (s, 0.3H, cmpd B), 4.36-4.51 (m, 2.6H, cmpd A/B CH$_3$CH$_2$), 4.17-4.25 (m, 2H, cmpd A OCH$_2$), 4.06-4.13 (m, 0.6H, cmpd B OCH$_2$), 2.85-2.93 (m, 0.6H, cmpd B CH$_2$), 2.71 (t, J=6.53 Hz, 2H, cmpd A CH$_2$), 2.45 (s, 3H, cmpd A CH$_3$), 1.99-2.15 (m, 2.6H, cmpd A/B CH$_2$), 1.54-1.88 (m, 0.6H, cmpd B CH$_2$), 1.44 (t, J=7.12 Hz, 0.9H, cmpd B CH$_3$), 1.44 (t, J=7.12 Hz, 3H, cmpd A CH$_3$); $^{13}$C NMR (75 MHz, CDCl$_3$) δ ppm 166.53, 165.01, 162.88, 159.21, 153.21, 143.48, 143.11, 142.72, 139.52, 136.74, 134.94, 130.12, 127.21, 73.82, 65.85, 61.61, 61.21, 33.74, 31.53, 24.97, 22.11, 21.48, 14.56, 14.28; Cmpd A: HRMS (M+Na) m/z, calcd for $C_{12}H_{15}NO_3Na$, 244.0950; found 244.0961; Cmpd B: HRMS (M+H) m/z, calcd for $C_{12}H_{16}NO_3$, 222.1130; found 222.1130.

Example 7

3,4-Dihydro-2H-pyrano[2,3-c]pyridine-6-carbaldehyde

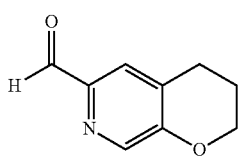

(VIII)

(a)
(3,4-Dihydro-2H-pyrano[2,3-c]pyridin-6-yl)methanol

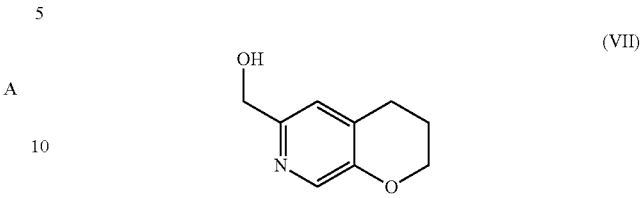

(VII)

To a vessel was added with stirring methyl 3,4-dihydro-2H-pyrano[2,3-c]pyridine-6-carboxylate (7.4 g, 1 eq) and tetrahydrofuran (THF) (32 mL). The mixture was heated to 55° C. whereupon 2M LiBH$_4$ in THF solution (20 mL, 1.05 eq.) was added over 1 h. The stirring continued at 55° C. until reduction was complete at which point the mixture was cooled to 45° C. and 6N HCl (37 mL) was carefully added to the mixture. The stirring was continued for 1 h then the mixture was cooled to 25° C. The pH was adjusted to ~9.5 to 10 with 50 wt % aqueous NaOH solution. The organics were extracted with 2-methyltetrahydrofuran (2×37 mL). The combined organic layers were concentrated under reduced pressure and crystallized to provide (3,4-dihydro-2H-pyrano[2,3-c]pyridin-6-yl)methanol as an off-white solid. $^1$H NMR (300 MHz, CDCl$_3$) δ ppm 8.10 (s, 1H), 6.91-6.99 (m, 1H), 4.65 (s, 2H), 4.18-4.29 (m, 2H), 3.42 (s, 1H), 2.79 (t, J=6.50 Hz, 2H), 1.96-2.12 (m, 2H); $^{13}$C NMR (75 MHz, CDCl$_3$) δ ppm 151.09, 150.39, 137.87, 131.40, 121.14, 66.51, 64.10, 24.22, 21.55; HRMS (M+H) m/z, calcd for $C_9H_{12}NO_2$, 166.0868; found, 166.0861.

(b) The Title Compound (3,4-Dihydro-2H-pyrano[2,3-c]pyridin-6-yl)methanol (300 g, 1.0 eq), DCM (1.5 L) and dimethyl sulfoxide (216 mL, 2.05 eq) were added with stirring to a vessel maintained at ~0 to 5° C. Triethylamine (858 mL, 4.1 eq) followed by solid pyridine sulphur trioxide (474 g, 2.0 eq) were slowly added to the mixture while maintaining the mixture temperature at ~0 to 7° C. The mixture was stirred at ~0 to 7° C. for ~5 to 8 h then quenched with aqueous 5 wt % NaHCO$_3$ solution (3 L) to form a biphasic mixture. The layers were separated and the aqueous layer was extracted with DCM (0.9 L). The combined organic layers were washed with aqueous 5 wt % citric acid (3.0 L) and brine (300 mL), dried over anhydrous sodium sulfate and filtered to provide the title compound in DCM solution. $^1$H NMR (300 MHz, CDCl$_3$) δ ppm 9.94 (s, 1H), 8.21-8.32 (m, 1H), 7.72 (s, 1H), 4.25-4.40 (m, 2H), 2.85 (t, J=6.50 Hz, 2H), 1.97-2.19 (m, 2H).

What is claimed is:
1. A process comprising the step of dehydrating a compound of Formula (I):

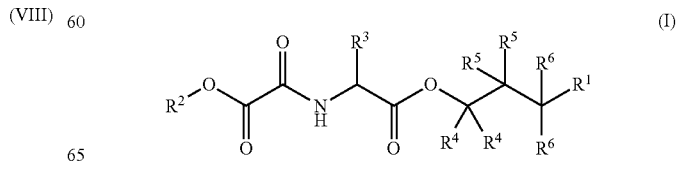

(I)

to form a compound of Formula (II):

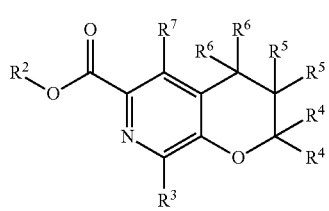

wherein $R^1$ is —CH=CH—$R^8$ or —CH$_2$—CH=CH—$R^9$;
$R^2$ is $C_1$-$C_4$-alkyl;
$R^3$ is H, $C_1$-$C_4$-alkyl, benzyl, or -phenyl-($R^{10}$)$_x$;
each $R^4$ is independently H, or $C_1$-$C_4$-alkyl;
each $R^5$ and each $R^6$ are independently H, $C_1$-$C_4$-alkyl, —O—$C_1$-$C_4$-alkyl, or —S—$C_1$-$C_4$-alkyl;
$R^7$ is $R^8$ or —CH$_2$—$R^9$;
$R^8$ is H, $C_1$-$C_4$-alkyl, or -phenyl-($R^{10}$)$_x$;
$R^9$ is H, $C_1$-$C_3$-alkyl, or -phenyl-($R^{10}$)$_x$;
each $R^{10}$ is independently halo, $C_1$-$C_6$-alkyl, —O—$C_1$-$C_4$-alkyl, or —S—$C_1$-$C_4$-alkyl; and
each x is independently 0, 1, or 2 wherein the process is carried out in the presence of an organic base and a dehydrating agent selected from Tf$_2$O or P$_2$O$_5$.

2. The process of claim 1 wherein $R^4$, $R^5$, and $R^6$ are each independently H or methyl; and the organic base is pyridine, triethylamine, or diisopropylethylamine.

3. The process of claim 2 wherein each of $R^4$, $R^5$, and $R^6$ is H; the dehydrating reagent is Tf$_2$O; and the organic base is used in an amount of at least 1 equivalent with respect to the compound of Formula (I) and less than the amount of the dehydrating reagent, in equivalents.

4. The process of claim 1 or which further comprises the steps of:
a) reducing the compound of Formula (II) with a suitable reducing reagent to form a compound of Formula (III):

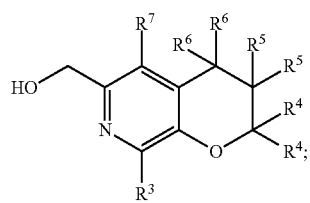

and
b) oxidizing the compound of Formula (III) with a suitable oxidizing reagent to form a compound of Formula (IV):

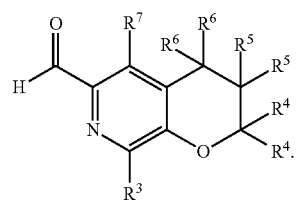

5. The process of claim 1 which further comprises the step of reducing the compound of Formula (II) with a suitable reducing reagent to form a compound of Formula (IV):

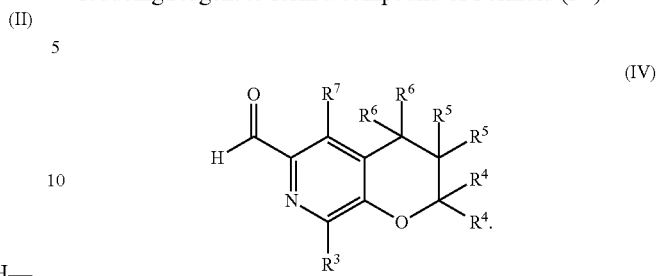

6. The process of claim 1 comprising the step of dehydrating a compound of Formula (V):

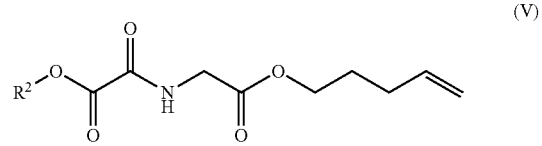

with a suitable dehydrating reagent to form a compound of Formula (VI):

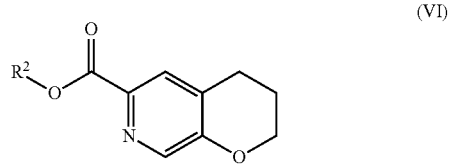

wherein $R^2$ is $C_1$-$C_4$-alkyl.

7. The process of claim 6 wherein the dehydrating reagent is Tf$_2$O or P$_2$O$_5$.

8. The process of claim 6 wherein the dehydrating reagent is Tf$_2$O; and $R^2$ is methyl or ethyl.

9. The process of claim 6 wherein the process is carried out in the presence of an organic base in an amount of at least 1 equivalent with respect to the compound of Formula (V) and less than the amount of the dehydrating reagent, in equivalents.

10. The process of claim 6 which further comprises the steps of:
a) reducing the compound of Formula (VI) with a suitable reducing reagent to form a compound of Formula (VII):

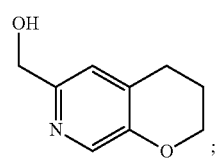

and
b) oxidizing the compound of Formula (VII) with a suitable oxidizing reagent to form a compound of Formula (VIII):

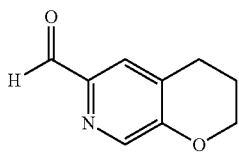

(VIII)

11. The process of claim 6 which further comprises the step of reducing the compound of Formula (VI) with a suitable reducing reagent to form a compound of Formula (VIII):

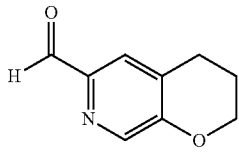

(VIII)

12. The process of claim 4 wherein the reducing reagent is diisobutylaluminium hydride, $LiAlH_4$, $LiBH_4$, or $NaBH_4$.

13. The process of claim 10 wherein the reducing agent is diisobutylaluminium hydride, $LiAlH_4$, $LiBH_4$, or $NaBH_4$.

14. The process of claim 12 wherein the reducing reagent is $LiBH_4$.

15. The process of claim 13 wherein the reducing reagent is $LiBH_4$.

16. The process of claim 4 wherein the oxidizing reagent is $MnO_2$, Swern oxidation reagents, 2-iodoxybenzoic acid, pyridine sulphur trioxide, or Dess-Martin periodinane.

17. The process of claim 10 wherein the oxidizing reagent is $MnO_2$, Swern oxidation reagents, 2-iodoxybenzoic acid, pyridine sulphur trioxide, or Dess-Martin periodinane.

18. The process of claim 16 wherein the oxidizing reagent is pyridine sulphur trioxide.

19. The process of claim 17 wherein the oxidizing reagent is pyridine sulphur trioxide.

20. The process of claim 5 wherein the reducing reagent is diisobutylaluminium hydride.

21. The process of claim 11 wherein the reducing reagent is diisobutylaluminium hydride.

* * * * *